(12) United States Patent
Howard

(10) Patent No.: US 6,865,444 B2
(45) Date of Patent: Mar. 8, 2005

(54) CONTAINER AND METHOD FOR DISPENSING TRANSDERMAL DOSAGE FORMS

(75) Inventor: Stephen Howard, Danbury, CT (US)

(73) Assignee: Euro-Celtique S.A., Luxembourg (LU)

(*) Notice: Subject to any disclaimer, the term of this patent is extended or adjusted under 35 U.S.C. 154(b) by 0 days.

(21) Appl. No.: 10/724,348

(22) Filed: Nov. 24, 2003

(65) Prior Publication Data

US 2004/0122554 A1 Jun. 24, 2004

Related U.S. Application Data

(63) Continuation-in-part of application No. PCT/US02/16272, filed on Mar. 22, 2002.
(60) Provisional application No. 60/292,602, filed on May 22, 2001.

(51) Int. Cl.[7] .............................................. G06F 17/00
(52) U.S. Cl. ........................ 700/237; 221/66; 221/102
(58) Field of Search ................................ 700/231, 237; 221/12, 66, 102

(56) References Cited

U.S. PATENT DOCUMENTS

| 1,649,435 A | * | 11/1927 | Woods ........................ 221/194 |
| 1,827,354 A | * | 10/1931 | Simon ......................... 221/15 |
| 2,182,615 A | * | 12/1939 | Johnson ...................... 206/359 |
| 3,809,287 A | * | 5/1974 | Muller-Scherak ............ 221/66 |
| 5,271,940 A | | 12/1993 | Cleary et al. |
| 5,694,919 A | | 12/1997 | Rubsamen et al. |
| 5,735,263 A | | 4/1998 | Rubsamen et al. |
| 5,928,194 A | | 7/1999 | Maget |

* cited by examiner

Primary Examiner—Khoi H. Tran
(74) Attorney, Agent, or Firm—Darby & Darby

(57) ABSTRACT

The present invention provides a two compartment device (10), and method of use, for the disposal of used transdermal dosage forms (26) and the dispensing of unused transdermal dosage forms (28). The first compartment (12) has a dosage form inlet (16) and a detector (20), and the second compartment (14) has a dosage form outlet (22) in communication with the detector (20). The detector (20) permits the dispensing of an unused transdermal dosage (28) form from the outlet (22).

42 Claims, 1 Drawing Sheet

CONTAINER AND METHOD FOR DISPENSING TRANSDERMAL DOSAGE FORMS

This application is a Continuation in Part of International application No. PCT/US02/16272, filed May 22, 2002, which claims priority from U.S. Provisional Application Ser. No. 60/292,602, filed May 22, 2001, which are incorporated herein by reference in their entirety.

BACKGROUND OF THE INVENTION

1. Field of the Invention

The present invention relates to a container and method for dispensing transdermal dosage forms.

2. Discussion of the Related Art

Transdermal dosage forms contain medication to be delivered to a patient. When prescribed by a physician, the transdermal dosage form (e.g., a transdermal patch) conventionally has a backing layer that is to be removed by the patient thereby revealing the medication and an adhesive so that the form will adhere to the patient's skin. The dosage form is placed on the patient, for example, on or near the bicep or on or near the chest, for a prescribed period of time so that the medication can be absorbed through the skin and delivered to the patient. At the end of the prescribed period of time, the used dosage form will generally contain residual amounts of the medication. Unfortunately, some people may illicitly abuse the medication contained in the used or unused dosage form for purposes other than those prescribed by a physician. These people often try to remove the medication from the dosage form, for example, by tearing open the dosage form and digesting the medication orally or by ingesting the medication parentally.

Therefore, it would be desirable to have a container and method for allowing the dispensing of transdermal dosage forms upon receipt of a used dosage form.

A further need exists for a container and method for discouraging abuse of transdermal dosage forms, such that when the medication is taken as directed, the medicament within is administered as intended, but when abused, the delivery of another unused transdermal dosage form is prevented.

SUMMARY OF THE INVENTION

Thus, it is an object of the present invention to provide a container and method for dispensing a transdermal dosage forms.

It is an object of further embodiments of the present invention to provide a container and method that prevents misuse of the medicament within the dosage form by not dispensing an used dosage form unless a non tampered dosage form has been received.

In accordance with a currently preferred exemplary embodiment the container and method includes a container for dispensing transdermal dosage forms comprising a housing that has a first compartment and a second compartment. The first compartment has an inlet of a sufficient size to receive a used transdermal dosage form. The second compartment has an outlet of a sufficient size to dispense an unused transdermal dosage form. A detector of used transdermal dosage forms is placed proximate to the inlet to permit the dispensing of an unused transdermal dosage form from the outlet.

In accordance with another currently preferred exemplary embodiment the container and method includes providing a patient with a first container for receiving used transdermal dosage forms and dispensing unused transdermal dosage forms and rewarding the patient upon the return of the container with used transdermal dosage forms.

In accordance with another currently preferred exemplary embodiment the container and method includes a device for the regulated dispensing of medication including a container having a first compartment and a second compartment. A detection device is disposed in relation to the first compartment. The first compartment comprises a used dosage form inlet that is unidirectional. The detection device determines the presence of a used dosage form at the used dosage form inlet and generates a data signal in response to the recognition of the used dosage form. An inlet door is selectively opened and closed in response to the data signal received from the detection device to access the used dosage form inlet. The detection device generates a second data signal in response to the used dosage form identified at the used dosage form inlet and disposed in the first compartment. The detection device transmitting the second data signal to the second compartment, the second compartment includes an unused dosage form outlet that is unidirectional and dispenses an unused dosage form. An outlet door is selectively opened and closed in response to the second data signal received from the detection device to access the unused dosage form outlet.

In accordance with another currently preferred exemplary embodiment the system and method includes dispensing an unused transdermal dosage forms and receiving used transdermal dosage forms. A container having a first compartment for receiving used transdermal dosage forms and a second compartment for dispensing unused transdermal dosage forms is provided. A used transdermal dosage form proximate to an inlet of the first compartment is scanned to verify that a used transdermal dosage form is being receiving in the first compartment. An outlet mechanism of the second compartment receives a communication signal that a used transdermal dosage form has been receiving in the first compartment. An unused transdermal dosage form is dispensed from an outlet of the second compartment.

The present invention also provides a deposit system for transdermal dosage forms that dissuades abuse of used transdermal dosage forms and provides an incentive to return used dosage forms to a dispensing medical professional or other appointed person or agent. The method includes (a) providing to a patient a kit comprising a dispenser for used transdermal dosage form(s) and a supply of transdermal dosage forms; and (b) requiring the patient to return the dispenser when the dispenser has been used in order to obtain a new dispenser and a further supply of transdermal dosage forms, wherein the patient is rewarded for returning the used dispenser.

The dispenser provided to the patient may be a compartmentalized dispenser, such as that described above, or any other disposal and dispensing system for transdermal dosage forms.

The transdermal dosage form, in accordance with one embodiment of the present invention, includes detection indicia, e.g., a bar code or hologram that is readable by a detector contained in a dispensing device, such as that described above.

BRIEF DESCRIPTION OF THE FIGURES

The above and still further objects, features and advantages of the present invention will become apparent upon consideration of the following detailed description of spe

DESCRIPTION OF THE INVENTION

Figure 1:
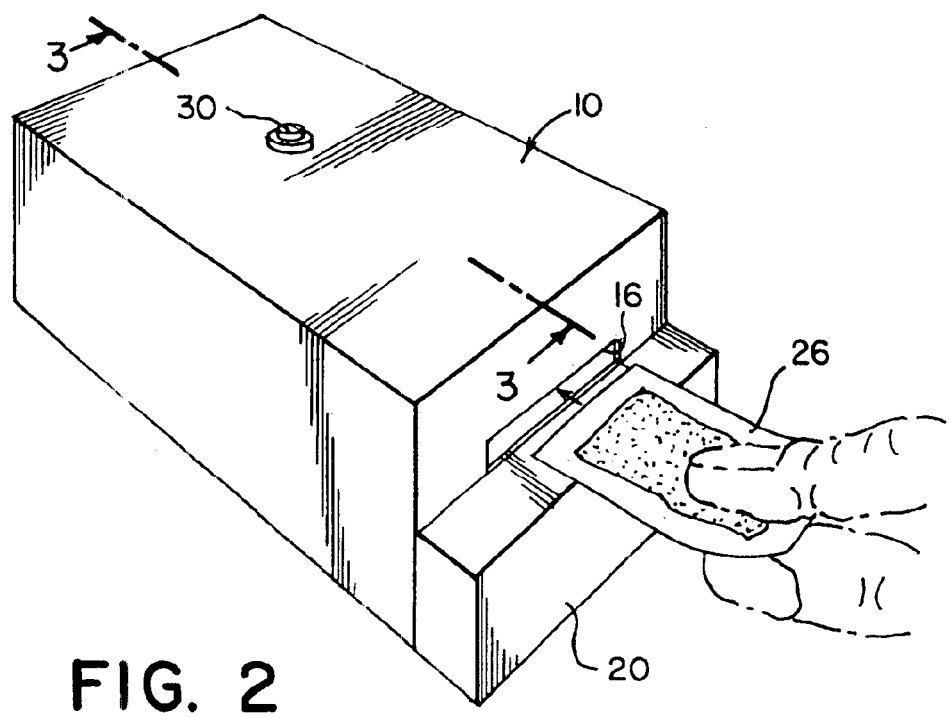
- FIG. 1 is a perspective view showing a container about to receive a used transdermal dosage form in accordance with the present invention.
Figure 2:
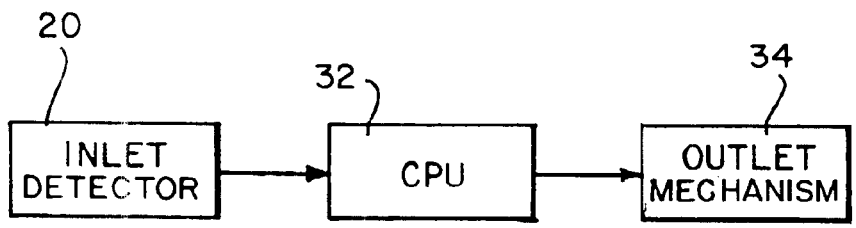
FIG. 2 shows a schematic of the control mechanism for operating the container of FIG. 1.
Figure 3:
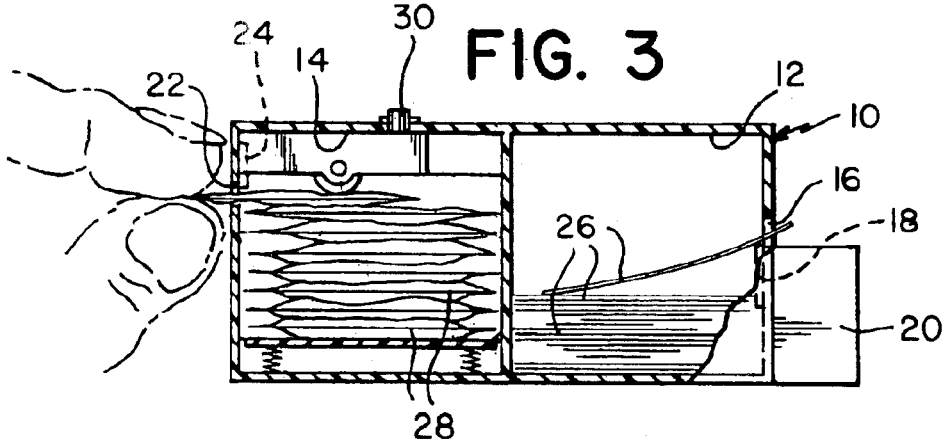
FIG. 3 shows the container of FIG. 1 dispensing an unused dosage form.

Referring now to FIGS. 1–3, a system for depositing used transdermal dosage forms and dispensing unused transdermal dosage forms in accordance with the present invention is illustrated. The system includes a container 10 having a first compartment 12 and a second compartment 14. First compartment 12 has a used dosage form inlet 16 that is selectively opened and closed by an inlet door 18. A detection device 20 is illustrated as being disposed inside compartment 12, but may be disposed external to compartment 12. Second compartment 14 has an unused dosage form outlet 22 that is selectively opened and closed by an outlet door 24. Inlet 16 is unidirectional and is adapted to receive a used transdermal dosage form 26. Inlet door 18 opens when detector 20 detects the presence of a used transdermal dosage form at the inlet.

The used and unused dosage forms both contain an identification, that is preferably tamperproof. The tamperproof identification is read by the detection device to identify the presence of the dosage form. Tamperproof identification may contain a serial number, a patient identification number, a dosage amount, the date and time the dose was dispensed, and/or a refill date. The tamperproof identification can be a barcode or a hologram. It can also be an electromagnetic transmitter that emits a signal that the detection device receives or it can transmit a magnetic field that will be detected. The tamperproof identification can also have a specific form or shape and only that specific shape (a "key form") will be permitted into the used dosage form inlet.

The detection device may be a processor to analyze the signal transmitted from the tamperproof identification. The detection device can compare the information contained in the signal to a pre-established set of parameters. For example, certain unused dosages, for a particular patient, should be dispensed every 3 days. The detection device may read the date and time the used dosage form was dispensed and allow or deny an unused dosage form to be dispensed based on whether 3 days have elapsed. Additionally, the second compartment may contain unused dosage forms containing differing drugs and/or dosage strengths. The processor may determine the proper drug and/or dosage strength from the signal and dispense the appropriate unused dosage form. Additionally, the processor may be pre-programmed to dispense a change in dosage strength and/or drugs depending on a pre-programmed prescription regiment based on the patent identification number read from the tamperproof identification.

The detection device may be disposed inside or outside the first compartment depending on the type of tamperproof identification and location of the device. The detection device can first detect the used dosage form and then open the inlet door upon recognition and allow the used dosage form to be inserted into used dosage form inlet. Alternately, the used dosage form inlet may contain the detection device and determine if inlet door should be selectively opened to allow the used dosage form to enter the first compartment.

Outlet 22 is also unidirectional and is adapted to dispense an unused dosage form 28 only after receiving a signal from the detector that a used dosage form has been received at inlet 16 and stored in first compartment 12. In certain embodiments, the first time an unused dosage form is to be dispensed, the system will not require the receipt of a used dosage form at inlet 16. The system may provide a "first dispense only" button 30 on container 10 which will permit the dispensing of an unused dosage form only for the initial dispensing of dosage forms. Thereafter, actuation of button 30 will not result in dispensing of an unused dosage form 28 from compartment 14, and unused dosage forms will be dispensed only if a used dosage form has been received and properly detected in compartment 12. Alternatively the dispensing professional (e.g., a pharmacist), may provide the patient with the first unused dosage form. The pharmacist can then activate container 10 to be set to recognize that first dosage form and upon receipt thereof to dispense another unused dosage form so long as all other requirements have been met.

In practice, after the dispensing of the first dosage form, the user may bring a used transdermal dosage form into contact with or close proximity to detector 20. If the detector recognizes the dosage form as such, the inlet door will open in order for the user to place the used dosage form within the first compartment, and the detector via a CPU 32 will send a signal to the outlet door mechanism 34 in the second compartment, which will open to release an unused transdermal dosage form (see FIG. 2). For example, as discussed above, some people illicitly abuse the medication contained within a used or unused dosage form. In an attempt to prevent this abuse, the dosage forms may include a barcode placed on a portion of the dosage form that would become irreparably damaged should the user try to tear open the dosage form or otherwise tamper with the dosage form. Of course, one skilled in the art will readily recognize that numerous other tamper proof devices may be used, which device can be detected by detector 20 before communicating a signal to outlet 22, 24 for dispensing another unused dosage form.

The outlet mechanism 22, 24 may include, as illustrated in the exemplary embodiment shown in FIG. 3, a spring biased unused dosage form support plate 32. Plate 32 is supported and biased in the upper direction by springs 34. The outlet mechanism may further include a roller 36 that is selectively actuated by CPU 32 to dispense an unused dosage form 28 through outlet 22, as illustrated in FIG. 3.

Both the inlet and outlet may be sized and configured to receive the variety of sizes of transdermal dosage forms that are being used at any given time. Alternatively, the inlet and outlet can be sized and configured to receive and dispense only one size of transdermal dosage forms. Additionally, both the first compartment 12 and second compartment 14 are of a sufficient size to house the number of used and unused dosage patches to be stored and dispensed, respectively. Therefore, both the inlet and outlet preferably have dimensions that are suitable for transport of a patch therethrough, e.g. approximately 15–150 mm diameter for round systems and 15×15–150×150 mm for square/rectangular, and the height of these devices should not exceed 10 mm. Currently, patches are packaged in individual envelopes in sizes typically ranging from 50×50 mm to 50×80 mm, with a thickness of less than 5 mm. Further, both the inlet and outlet are preferably unidirectional, i.e., the inlet only allows passage of a dosage form into the first compartment, whereas the outlet only allows passage of a dosage form out from the second compartment (and the inlet will not allow a used patch to be taken out of the first compartment through the inlet, nor will the outlet allow a patch to be inserted into the second compartment through the outlet). Moreover, if an object other than a transdermal patch is placed at the inlet, the detector will preferably not initiate a signal that will allow the inlet or outlet doors to open to receive the object and dispense an unused patch. Of course, if the detector were not to scan the object until after it has been placed in first compartment 12, container 10 would receive the object, but no signal would be sent to outlet 22, 24, thereby preventing an unused dosage form from being released.

The detector may be adapted to detect the presence of a transdermal patch by any device necessary as are known to those skilled in the art. For example, the patch may be impregnated with a hologram or other signal, such as a bar code, that is detected by the detector. Alternatively, a contact switch can be used to detect the insertion of a used transdermal dosage form in the inlet, and/or the detector may include an activating signal that a used transdermal patch has been placed in contact with the inlet. Further, a transdermal dosage form is also contemplated that includes a detection indicia, e.g., a hologram or bar code, that may be detected by a detector in a dispenser such as that described above.

In one embodiment, the disposal system is designed to accept transdermal patches that are folded. The disposal system can also be designed so that it only accepts folded transdermal patches. For example, the transdermal patch can be folded so that one half of the adhesive side of the patch is brought into contact with the other half. A strong adhesive would then make it difficult to re-open the folded patch. In patches where the medicament is in close contact, or mixed, with the adhesive, folding could make the medicament very difficult to retrieve or extract from the folded patch. In other types of patches, where the medicament is contained in a pouch inside of the patch, folding could result in the release of an inactivating agent (see below) via a suitable mechanism, thereby preventing retrieval or extraction of active medicament from a disposed patch. To detect that a patch is properly folded when it is inserted into the disposal system, the non-adhesive side can be suitably marked with, e.g., barcodes or holograms as described above, at different ends of the non-adhesive side, so that the detector unit registers a marking on both sides of the folded patch. Additionally, the inlet of a disposal system for folded patches can be smaller than a disposal system for non-folded patches, since the folded patch will be smaller than the original patch. For example, a disposal system based on folding a patch in half before insertion can have an inlet end about half as wide as the original patch.

Alternatively, the disposal system may also include one or more inactivating agents in either the first or second compartment. In a preferred embodiment, an inactivating agent is placed in the first compartment, such that when the user places a used transdermal dosage form in the first compartment, the inactivating agent is released and the agent inactivates any unused medicament contained within the used dosage form. Alternatively, the inactivating agent may not be activated until all used dosage forms have been deposited in the first compartment. Further, an inactivating agent may also be included in the second compartment, wherein an opening to the container is in communication with the outlet door and detector. In practice, if the outlet door is tampered with and/or the detector is not activated by placing a used dosage form at the inlet, the inactivating material is released inside the second compartment, thereby inactivating the medicament contained within the unused dosage forms.

The inactivating agent may be selected from the group consisting of an indelible dye, a biological inactivating agent, a chemical inactivating agent, a denaturing inactivating agent, an electrical inactivating agent, a magnetic inactivating agent, a mechanical inactivating agent, a cross-linking inactivating agent, rat or human mu-opioid receptor, opioid neutralizing antibodies, a narcotic antagonist, irritating or dysphoric agents, or any combination thereof.

While the dosage form may be formulated for virtually any medicament, in a preferred embodiment, the medicament is a controlled substance such as an opioid, benzodiazapene, fentanyl, buprenorphine or etorphine, and the inactivating agent is an opioid or benzodiazepene antagonist or a noxious agent, e.g., an emetic. In this regard, reference is made U.S. Pat. No. 4,806,341 to Chien, which discloses possible medicaments and inactivating agents that may be used in the dosage forms used in the present invention.

Under the United States Controlled Substance Act, opioids and other controlled substances are broken into five (5) schedules of varying abuse potential. Substances in Schedule I have no current clinical benefit in the United States, but have the highest potential for abuse. Schedules II–V have decreasing levels of abuse, respectively. Examples of Schedule II substances include, but are not limited to, opium, morphine, and cocaine; Schedule III substances include, but are not limited to, certain barbiturates and nalorphine; Schedule IV include, but are not limited to, phenobarbital and certain benzodiazepines; and Schedule V include, but are not limited to, preparations which use opioids.

There are a variety of ways in which an inactivating agent can render the medicament unavailable through inactivation; for example, chemical inactivation or alteration of the receptor binding site of the medicament; electrical inactivation or alteration of the receptor binding site of the medicament; magnetic inactivation or alteration of the receptor binding site of the medicament; mechanical inactivation or alteration of the receptor binding site of the medicament; biounavailability; physical unavailability; loss of appeal of the medicament to the abuser, such as for example, an inactivating agent which creates an intolerably bad taste or an intolerable reaction such as extreme nausea or the like; or something similar thereto. One or more inactivating agent(s) may be used. Further, if the medicament were an opioid, the inactivating agent could be a chemical or denaturing agent that would alter residual opioid molecules in the dosage form and make them inactive. The inactivating agent could be an opioid receptor that would bind the residual opioid into an insoluble ligand-receptor complex. The inactivating agent could also be an opioid receptor antagonist, preferably with greater specificity and/or affinity for the receptor than the opioid, which would be isolated or delivered with the residual opioid upon misuse and compete with the residual opioid for the opioid receptor, thereby defeating the purpose of misusing the opioid. This would render the residual opioid useless in vivo. The inactivating agent could also physically sequester the medicament such as, for example, in an impermeable microsphere or in a permanently bound matrix. Similarly, the inactivating agent could be a non-opioid with distressing or dysphoric properties if absorbed that made abuse unappealing.

The dosage form may also contain a detection material that is also released when the dispenser is tapered with, making it visible to the user that the dosage form has been misused.

Further, the amount of inactivating agent will depend upon the medicament and the amount of residual medicament that is expected in a particular dosage form. Such amounts can also be determined by those skilled in the art by methods such as establishing a matrix of amounts and effects. However, such amounts should be those amounts effective to achieve the results sought, i.e., inactivation of the residual medicament or the rendering undesirable of a therapeutic drug of abuse.

Non-limiting examples of medicaments that may be used in the present invention are fentanyl, buprenorphine, etorphine and related opioids of sufficient potency to allow transdermal usage, or any combinations thereof. Non-limiting examples of inactivating agents include the rat or human mu-opioid receptor; opioid-neutralizing antibodies; narcotic antagonists such as naloxone, naltrexone and nalmefene; dysphoric or irritating agents such as scopolamine, ketamine, atropine or mustard oils; or any combinations thereof.

The present invention also provides a deposit system for transdermal dosage forms that dissuades abuse of used transdermal dosage forms and provides an incentive to return used dosage forms to a dispensing medical professional or other appointed person or agent. The method includes (a) providing to a patient a kit comprising a dispenser for used transdermal dosage form(s) and a supply of transdermal dosage forms; and (b) requiring the patient to return the dispenser when the dispenser has been used in order to obtain a further supply of transdermal dosage forms, wherein the patient is rewarded for returning the used dispenser.

For example, the deposit system may comprise providing to a patient a kit comprising a dispenser and a supply of dosage forms at a first price, and when the patient returns the used dispenser, an additional dispenser and supply of dosage forms is provided at a second price, wherein the second price is reduced relative to the first price. Alternatively, the reward system may include providing the patient with coupons upon return of the used dispenser, wherein the coupons reduce the cost of subsequent purchases of, e.g., additional dosage forms.

The container provided to the patient may be a compartmentalized dispenser, such as that described above, or any other disposal system for transdermal dosage forms. The container can be made of sturdy construction so that it is tamper proof. Additionally, window(s) may be provided so that the user can determine how many unused dosage forms remain and how many used dosage forms have been deposited. In addition, a pharmacist can use the window to confirm that the first compartment is actually full of used patches before providing the patient with another container. In accordance with further embodiments, the container can identify the user, alternatively or in addition to the dosage form. For example, the container can accept a special encoded tag of the patient, or may even scan the patient directly by a hand/finger/retina, (etc.) scanner to identify the patient. Alternatively, the container could include a camera and the detector can perform a visual inspection. The container can also monitor how many patches are received and can communicate this information, for example, by the internet, to inform a pharmacist or other monitor that the container is running low.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated by reference.

What is claimed is:

1. A container for dispensing transdermal dosage forms comprising:
   a housing having a first compartment and a second compartment, the first compartment having an inlet of a sufficient size to receive a used transdermal dosage form, the second compartment having an outlet of a sufficient size to dispense an unused transdermal dosage form, and
   a detector of used transdermal dosage forms placed in the inlet to permit the dispensing of an unused transdermal dosage form from the outlet.

2. The container of claim 1, wherein the second compartment contains a plurality of unused transdermal dosage forms.

3. The container of claim 2, wherein the second compartment contains a plurality of unused patches.

4. The container of claim 1, further comprising a CPU in communication with the detector, the CPU permits receipt of a used transdermal dosage form through the inlet.

5. The container of claim 4, wherein the CPU permits receipt of the used transdermal dosage form through the inlet before an unused transdermal dosage form is dispensed through the outlet.

6. The container of claim 1, wherein the detector comprises a bar code scanner.

7. The container of claims 1, wherein the detector comprises a hologram reader.

8. The container of claim 1, wherein the detector detects the placement of a used untampered transdermal dosage form proximate to said inlet.

9. The container of claim 1, wherein said first compartment is sealed from said second compartment.

10. The container of claim 2, wherein the transdermal dosage forms contains an active agent.

11. The container of claim 10, wherein the active agent is an opioid.

12. A container for dispensing transdermal dosage forms comprising:
    a housing having a first compartment and a second compartment, the first compartment having an inlet of a sufficient size to receive a used transdermal dosage form, the second compartment having an outlet of a sufficient size to dispense an unused transdermal dosage form, and
    means for detecting when a used transdermal dosage form has been placed in the inlet to permit the dispensing of an unused transdermal dosage form from the outlet.

13. The container of claim 12, wherein the second compartment contains a plurality of unused transdermal dosage forms.

14. The container of claim 13, wherein the second compartment contains a plurality of unused patches.

15. The container of claim 12, further comprising a CPU in communication with the detector, the CPU having means for permitting receipt of a used transdermal dosage form through the inlet.

16. The container of claim 15, wherein the CPU having means for permitting receipt of the used transdermal dosage form through the inlet before an unused transdermal dosage form is dispensed through the outlet.

17. The container of claim 12, wherein the means for detecting includes scanning a bar code.

18. The container of claims 12, wherein the means for detecting includes reading a hologram.

19. The container of claim 12, wherein the means for detecting detects the placement of a used untampered transdermal dosage form proximate to said inlet.

20. The container of claim 12, wherein said first compartment is sealed from said second compartment.

21. The container of claim 13, wherein the transdermal dosage forms contains an active agent.

22. The container of claim 21, wherein the active agent is an opioid.

23. A method of dispensing unused transdermal dosage forms comprising the steps of:
 (a) providing a patient with a first container for receiving used transdermal dosage forms to permit dispensing unused transdermal dosage forms; and
 (b) rewarding the patient upon the return of the container with used transdermal dosage forms.

24. The method according to claim 23, wherein said rewarding step includes selling said new container at a lower price than the cost of said first container.

25. The method according to claim 23, wherein said rewarding step includes providing said patient with coupons.

26. The method according to claim 23, wherein said rewarding step includes providing said patient with funds.

27. The method according to claim 23, wherein the unused transdermal dosage form contains an active agent.

28. The method according to claim 27, wherein the active agent is an opioid.

29. A method of dispensing unused transdermal dosage forms comprising the steps of:
 (a) providing a patient with (i) a first container for receiving used transdermal dosage forms to permit dispensing unused transdermal dosage forms; and (ii) means of rewarding the patient upon the return of the container with used transdermal dosage forms.

30. The method according to claim 29, wherein said means of rewarding includes selling said new container at a lower price than the cost of said first container.

31. The method according to claim 29, wherein said means of rewarding includes providing said patient with coupons.

32. The method according to claim 29, wherein said means of rewarding includes providing said patient with funds.

33. A device for the regulated dispensing of medication comprising:
 a container having a first compartment and a second compartment;
 a detection device disposed in relation to said first compartment, said first compartment comprising:
  an used dosage form inlet being unidirectional, wherein said detection device determining the presence of a used dosage form at said used dosage form inlet and generating a data signal in response to the recognition of said used dosage form;
  an inlet door being selectively opened and closed in response to said data signal received from said detection device to access said used dosage form inlet, said detection device generating a second data signal in response to said used dosage form being identified at said used dosage form inlet and disposed in said first compartment, said detection device transmitting said second data signal to said second compartment,
 said second compartment comprising:
  an unused dosage form outlet being unidirectional and dispensing an unused dosage;
  an outlet door being selectively opened and closed in response to said second data signal received from said detection device to access said unused dosage form outlet.

34. The device according to claim 33, wherein said detection device is disposed within said first compartment.

35. The device according to claim 33, wherein said used dosage being a transdermal patch and wherein said unused dosage being a transdermal patch.

36. The device according to claim 33, wherein said used dosage further comprises a tamperproof identification being detected by said detection device.

37. The device according to claim 36, wherein said tamperproof identification comprises at least one of a barcode, a hologram, an electromagnetic transmitter and a key form.

38. A method of dispensing an unused transdermal dosage forms and receiving used transdermal dosage forms, said method comprising the steps of:
 providing a container having a first compartment for receiving used transdermal dosage forms and a second compartment for dispensing unused transdermal dosage forms;
 scanning a used transdermal dosage form proximate to an inlet of the first compartment to verify that a used transdermal dosage form is being receiving in the first compartment;
 communicating with an outlet mechanism of the second compartment that a used transdermal dosage form has been receiving in the first compartment; and
 dispensing an unused transdermal dosage form from an outlet of the second compartment.

39. The method according to claim 38, wherein the scanning step verifies that a used untampered transdermal dosage form is being received in the first compartment.

40. The method according to claim 39, wherein the used transdermal dosage form is received in the first compartment before an unused transdermal dosage form is dispensed from the outlet of the second compartment.

41. The method according to claim 40, wherein said dispensing step occurs only after a predetermined amount of time has elapsed since the immediate previous dispensing of an unused transdermal dosage form.

42. The method according to claim 38, wherein a medical dispensing technician fills the second compartment with unused transdermal dosage forms.

* * * * *